US011013759B2

(12) United States Patent
Wittke et al.

(10) Patent No.: US 11,013,759 B2
(45) Date of Patent: *May 25, 2021

(54) COMPOSITIONS FOR ENHANCING IMMUNE FUNCTION IN A PEDIATRIC SUBJECT

(71) Applicant: Mead Johnson Nutrition Company, Glenview, IL (US)

(72) Inventors: Anja Wittke, Boston, MA (US); Hugh Lipmann, Seattle, WA (US)

(73) Assignee: MEAD JOHNSON NUTRITION COMPANY, Glenview, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/833,133

(22) Filed: Aug. 23, 2015

(65) Prior Publication Data

US 2016/0317567 A1 Nov. 3, 2016

Related U.S. Application Data

(63) Continuation of application No. 12/790,670, filed on May 28, 2010, now abandoned.

(51) Int. Cl.
| | |
|---|---|
| *A61K 31/716* | (2006.01) |
| *A23L 33/00* | (2016.01) |
| *A23L 33/17* | (2016.01) |
| *A23L 33/135* | (2016.01) |
| *A23L 33/12* | (2016.01) |
| *A23L 33/10* | (2016.01) |
| *A61K 9/00* | (2006.01) |
| *A61K 31/202* | (2006.01) |
| *A61K 35/745* | (2015.01) |
| *A61K 35/747* | (2015.01) |
| *A61K 36/064* | (2006.01) |
| *A61K 47/26* | (2006.01) |
| *A61K 47/42* | (2017.01) |
| *A61K 47/44* | (2017.01) |
| *A61K 35/00* | (2006.01) |

(52) U.S. Cl.
CPC ............ *A61K 31/716* (2013.01); *A23L 33/10* (2016.08); *A23L 33/12* (2016.08); *A23L 33/135* (2016.08); *A23L 33/17* (2016.08); *A23L 33/30* (2016.08); *A23L 33/40* (2016.08); *A61K 9/0095* (2013.01); *A61K 31/202* (2013.01); *A61K 35/745* (2013.01); *A61K 35/747* (2013.01); *A61K 36/064* (2013.01); *A61K 47/26* (2013.01); *A61K 47/42* (2013.01); *A61K 47/44* (2013.01); *A23V 2002/00* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 4,962,094 | A | 10/1990 | Jamas et al. |
| 5,028,703 | A | 7/1991 | Jamas et al. |
| 5,032,401 | A | 7/1991 | Jamas et al. |
| 5,037,972 | A | 8/1991 | Jamas et al. |
| 5,082,936 | A | 1/1992 | Jamas et al. |
| 5,250,436 | A | 10/1993 | Jamas et al. |
| 5,322,841 | A | 6/1994 | Jamas et al. |
| 5,374,657 | A | 12/1994 | Kyle |
| 5,397,591 | A | 3/1995 | Kyle et al. |
| 5,397,773 | A | 3/1995 | Donzis |
| 5,488,040 | A | 1/1996 | Jamas et al. |
| 5,504,079 | A | 4/1996 | Jamas et al. |
| 5,506,124 | A | 4/1996 | Jamas et al. |
| 5,519,009 | A | 5/1996 | Donzis |
| 5,532,223 | A | 7/1996 | Jamas et al. |
| 5,550,156 | A | 8/1996 | Kyle |
| 5,576,015 | A | 11/1996 | Donzis |
| 5,607,677 | A | 3/1997 | Jamas et al. |
| 5,622,939 | A | 4/1997 | Jamas et al. |
| 5,622,940 | A | 4/1997 | Ostroff |
| 5,633,369 | A | 5/1997 | Jamas et al. |
| 5,663,324 | A | 9/1997 | Jamas et al. |
| 5,702,719 | A | 12/1997 | Donzis |
| 5,705,184 | A | 1/1998 | Donzis |
| 5,741,495 | A | 4/1998 | Jamas et al. |
| 5,783,569 | A | 7/1998 | Jamas et al. |
| 5,811,542 | A | 9/1998 | Jamas et al. |
| 5,817,643 | A | 10/1998 | Jamas et al. |
| 5,849,720 | A | 12/1998 | Jamas et al. |
| 6,020,324 | A | 2/2000 | Jamas et al. |
| 6,046,323 | A | 4/2000 | Park |
| 6,084,092 | A | 7/2000 | Wakshull et al. |

(Continued)

FOREIGN PATENT DOCUMENTS

| | | |
|---|---|---|
| CN | 101353383 | 1/2009 |
| JP | 2006187258 | 7/2006 |

(Continued)

OTHER PUBLICATIONS

Cunningham, Marion, The Fannie Farmer Cookbook, 13th Edition, Alfred A Knopp, 2005, pp. 615.*
Bowden, Jonny, The 150 Healthiest Food on Earth, Fair Winds Press, Jan. 1, 2007, pp. 76-77.*
Particulate definition, https://dictionary.com/browse/particulate, retrieved online Mar. 27, 2019 (Year: 2019).*
Aguilar-Uscanga, B., et al., A study of the yeast cell wall composition and structure in response to growth conditions and mode of cultivation, Letters in Applied Microbiology 2003, 37, 268-274.
Akramiene, D., et al., Effects of β-glucans on the immune system, Medicina (Kaunas) 2007; 43(8): 597-606.
Allendorf, D., et al., C5a-Mediated Leukotriene B4-Amplified Neutrophil Chemotaxis Is Essential in Tumor Immunotherapy Facilitated by Anti-Tumor Momoclonal Antibody and β-Glucan1, The Journal of Immunology, 2005, 174: 7050-7056.

(Continued)

*Primary Examiner* — Hong T Yoo
(74) *Attorney, Agent, or Firm* — Troutman Pepper Hamilton Sanders LLP; Ryan Schneider; Chris N. Davis (57) ABSTRACT

Compositions for and methods of increasing the number of neutrophils in a pediatric subject and stimulating the immune system of a pediatric subject.

21 Claims, 3 Drawing Sheets

(56) References Cited

U.S. PATENT DOCUMENTS

| | | | |
|---|---|---|---|
| 6,090,938 | A | 7/2000 | Wakshull et al. |
| 6,110,692 | A | 8/2000 | Wakshull et al. |
| 6,117,850 | A | 9/2000 | Patchen et al. |
| 6,143,731 | A | 11/2000 | Jamas et al. |
| 6,168,821 | B1 * | 1/2001 | Castleberry ............... A23L 2/02 426/18 |
| 6,294,321 | B1 | 9/2001 | Wakshull et al. |
| 6,369,216 | B1 | 4/2002 | Patchen et al. |
| 6,413,715 | B2 | 7/2002 | Wakshull et al. |
| 6,630,310 | B1 | 10/2003 | Wakshull et al. |
| 7,022,685 | B2 | 4/2006 | Patchen et al. |
| 7,572,474 | B2 | 8/2009 | Petschow et al. |
| 2003/0072865 | A1 | 4/2003 | Bindels et al. |
| 2004/0191234 | A1 | 9/2004 | Haschke |
| 2010/0056471 | A1 | 3/2010 | Boulat et al. |

FOREIGN PATENT DOCUMENTS

| | | |
|---|---|---|
| JP | 2007254425 | 10/2007 |
| WO | 20020047612 | 6/2002 |
| WO | 2006088923 | 8/2006 |
| WO | 2007035007 | 3/2007 |
| WO | 2008115046 | 9/2008 |

OTHER PUBLICATIONS

Babicek, K., et al., Toxicological assessment of a particulate yeast (1,3/1,6)-β-D-glucan in rats, Food and Chemical Toxicology, 45 (2007) 1719-1730.

Babineau, T., et al., Randomized Phase I/II Trial of a Macrophage-Specific Immunomodulator (PGG-Glucan) in High Risk Surgical Patients, Annals of Surgery vol. 220, No. 5, 601-609.

Babineau, T., et al., A Phase II Multicenter, Double-Blind, Randomized, Placebo-Controlled Study of Three Dosages of an Immunomodulator (PGG-Glucan) in High-Risk Surgical Patients, Arch Surg. 1994;129:1204-1210.

Berner, M.D., et al., "IFN-y primes macrophages for enhanced TNF-a expression in response to stimulatory and non-stimulatory amounts of microparticulate B-glucan," Immunology Letters 98 (2005) 115-122.

Bobak, et al., Maternity and Gynecologic Care, 4th Edition, 1989, p. 470.

Boehm, et al., Structural and Functional Aspects of Prebiotics Used in Infant Nutrition1,2, J. Nutr. 138: 1818S-1828S, 2008.

Borzelleca, J. et al., Expert Panel Consensus Statement Concerning the Generally Recognized as Safe (GRAS) Status of Yeast Beta-Glucan for Use as a Food Ingredient, Biothera, Inc., Aug. 29, 2007, p. 1-25.

Brown, G., Fungal β-Glucans and Mammalian Immunity, Immunity, vol. 19, 311-315, Sep. 2003.

Cox, D., et al., Mechanisms of Action of Wellmune WGP® in Immune Health, Biothera, Inc., Oct. 29, 2007.

Czop, J.K., & Austen, K.F. (1985). Properties of glycans that activate the human alternate complement pathway and interact with the human monocyte beta glucan receptor. J. Immuno. 135, 3388-3393.

Dellinger, E., et al., Effect of PGG-glucan on the Rate of Serious Postoperative Infection or Death Observed After High-Risk Gastrointestinal Operations, Arch Surg., 1999; 134:977-983.

Harler, M., et al., Promotion of Neutrophil Chemotaxis Through Differential Regulation of β1 and β2 Integrins1, The Journal of Immunology, 1999, 162: 6792-6799.

Hong, F., et al., β-Glucan Functions as an Adjuvant for Monoclonal Antibody Immunotherapy by Recruiting Tumoricical Granulocytes as Killer Cells, Cancer Research 63, 9023-9031, Dec. 15, 2003.

Hong, F., et al., Mechanism by Which Orally Administered β-1,3-Glucans Enhance the Tumoricidal Activity of Antitumor Monoclonal Antibodies in Murine Tumor Models1, The Journal of Immunology, 2004, 173: 797-806.

Hunter, K.W., et al., "Micorparticulate B-glucan upregulates the expression of B7.1, B7.2, B7-H1, but not B7-DC on cultured murine peritoneal macrophages," Immunology Letters 93 (2004) 71-78.

Hunter, K.W., et al., "Preparation of micorparticulate B-glucan from *Saccharomyces cerevisiae* for use in immune potentation," Letters in Applied Microbiology 2002, 335, 267-271.

Kaiser, A., et al., Synergism between Poly-(1-6)-β-D-Glucopyranose Glucan and Cefazolin in Prophylaxis of Staphylococcal Wound Infection in a Guinea Pig Model, Antimicrobial Agents and Chemotherapy, vol. 42, No. 9, Sep. 1998, p. 2449-2451.

Kalman, D., A randomized, double-blind placebo controlled trial of Wellmune WGP® for immune support during cold season, Experimental Biology 2008, Apr. 5-9, 2008—Abstract.

Kernodle, D., et al., Prophylactic Anti-Infective Activity of Poly-[1-6]-β-D-Glucopyranosyl-[1-3]-β-D-Glucopyranose Glucan in a Guinea Pig Model of Staphylococcal Wound Infection, Antimicrobial Agents and Chemotherapy, vol. 42, No. 3, Mar. 1998, p. 545-549.

Kournikakis, PhD, B., et al., Anthrax-Protective Effects of Yeast Beta 1,3 Glucans, Medscape General Medicine 5(1), 2003.

Kunz, et al., Oligosaccharides in Human Milk: Structure, Functional, and Metabolic Aspects, Ann. Rev. Nutr. 20: 699-722 (2000).

Li, B., et al., Yeast β-Glucan Amplifies Phagocyte Killing of iC3b-Opsonized Tumor Cells via Complement Receptor 3-Syk-Phosphatidylinositol 3-Kinase Pathway1, The Journal of Immunology, 2006, 177: 1661-1669.

Liang, J., et al., Enhanced clearance of a multiple antibiotic resistant *Staphylococcus aureus* in rats treated with PGG-glucan is associated with increased leukocyte counts and increased neutrophil oxidative burst activity, International Jounral of Immunopharmacology, 20 (1998) 595-614.

Newburg, Do the Binding Properties of Oligosaccharides in Milk Protect Human Infants from Gastrointestinal Bacteria?, J. Nutr. 217:S980-S984 (1997).

Onderdonk, A., et al., Anti-Infective Effect of Poly-β1-6-Glucotriosyl-β1-3-Glucopyranose Glucan in Vivo, Infection and Immunity, Apr. 1992, 60: 1642-1647.

Reichner, J., et al., Receptor-mediated phagocytosis of rat macrophages is regulated differentially for opsonized particles and non-opsonized particles containing β-glucan, Immunology, 2001, 104: 198-206.

Salvador, C., et al., Yeast-Derived β-Glucan Augments the Therapeutic Efficacy Mediated by Anti-Vascular Endothelial Growth Factor Monoclonal Antibody in Human Carcinoma Xenograft Models, Clin. Cancer Res 2008;14(4)1239-1247.

Tsikitis, V., et al., The Lectin-Like Domain of Complement Receptor 3 Protects Endothelial Barrier Function from Activated Neutrophils1, The Journal of Immunology, 2004, 173: 1284-1291.

Tzianabos, A, et al., Protection against Experimental Intraabdominal Sepsis by Two Polysaccharide Immunomodulators, The Journal of Infectious Diseases, 1998; 178:200-6.

Tzianabos, A, et al., Prophylaxis with the Immunomodulator PGG Glucan Enhances Antibiotic Efficacy in Rats Infected with Antibiotic-Resistant Bacteria, Annals New York Academy of Sciences, 1996, 797: 285-287.

Vetvicka, V., et al., Soluble β-Glucan Polysaccharide Binding to the Lectin Site of Neutrophil or Natural Killer Cell Complement Receptor Type 3 (CD11b/CD18) Generates a Primed State of the Receptor Capable of Mediating Cytotoxicity of iC3b-Opsonized Target Cells, J. Clin. Invest., 1996, 98: 50-61.

Walsh, D., Wellmune WGP® Reduced Fatigue and Infection Symptoms in Marathoners, Biothera, Inc., Nov. 6, 2007.

Walsh, D., Wellmune WGP® Reduces Incidence of Stress-Related Health Challenges, Biothera, Inc., Nov. 6, 2007.

Wellmune WGP® Physical Properties, undated.

Wellmune WGP® Insoluble Powder Product Sheet, Jul. 24, 2007.

Xia, Y., et al., The β-Glucan-Binding Lectin Site of Mouse CR3 (CD11b/CD18) and Its Function in Generating a Primed State of the Receptor That Mediates Cytotoxic Activation in Response to iC3b-Opsonized Target Cells1, The Journal of Immunology, 1999, 162: 2281-2290.

Chen et al. (2012) Methods Mol Biol 844:115-124.

Destin et al. ((2009) Early Hum Dev 85(8):531-5.

(56) References Cited

OTHER PUBLICATIONS

Berner, Mathew D. et al., "IFN-y primes macrophages for enhanced TNF-a expression in response to stimulatory and non-stimulatory amounts of microparticulate B-glucan," Immunology Letters, 2005, 98, pp. 115-122.

Hunter Jr., Kenneth, W. et al., "Microparticulate B-glucan upregulates the expression of B7.1, B7.2, B7-H1, but not B7-DC on cultured murine peritoneal macrophages," Immunology Letters, 2004, 93, pp. 71-78.

Hunter Jr., K.W. et al., "Preparation of microparticulate B-glucan from *Saccharomyces cerevisiae* for use in immune potentiation," Letters in Applied Microbiology, 2002, 35, pp. 267-271.

Williams, David L. et al., "Development of a water-soluble, sulfated (1-3)-B-D-glucan biological response modifier derived from *Saccharomyces cerevisiae*," Carbohydrate Research, 1992, 235, pp. 247-257.

\* cited by examiner

COMPOSITIONS FOR ENHANCING IMMUNE FUNCTION IN A PEDIATRIC SUBJECT

TECHNICAL FIELD

The present disclosure relates to nutritional compositions for enhancing immune function in a pediatric subject. More particularly, the disclosure relates to nutritional compositions having an effective amount of β-glucan in a milk-based matrix.

BACKGROUND ART

Infants and children are exposed to a variety of pathogens, and consequently, the incidence of infectious diseases peaks in the first 4 years of life. Newborns are generally protected by antibodies received through the placenta before birth and subsequently through breast milk after birth; yet newborns do not have mature immune systems and are often incapable of mounting an effective immune response. Indeed, on a cellular level, infants have a decreased ability to concentrate leukocytes where necessary. (*Maternity and Gynecologic Care*, Bobak, Jensen, Zalar, Fourth Edition, p. 470) Consequently, newborns are not able to limit invading pathogens due to a generalized hypofunction of their inflammatory and immune mechanisms. As such, improving the immune response in infants and/or children would provide an opportunity to reduce the incidence of infections and to maintain or improve the overall health of pediatric subjects.

The infant gut microflora is rapidly established in the first few weeks following birth, and it has a great impact on an infant's immune system. The nature of this intestinal colonization is initially determined by the host's early exposure to environmental sources of microbes as well as to the health of the infant. Whether the infant is breast-fed or formula-fed also has a strong influence on the intestinal bacterial population.

Human milk contains a number of factors that may contribute to the growth and population of the gut microflora of infants. Among these factors is a complex mixture of more than 130 different oligosaccharides that reach levels as high as 8-12 g/L in transitional and mature milk. Kunz, et al., *Oligosaccharides in Human Milk: Structure, Functional, and Metabolic Aspects*, Ann. Rev. Nutr. 20: 699-722 (2000). These oligosaccharides are resistant to enzymatic digestion in the upper gastrointestinal tract and reach the colon intact, where they then serve as substrates for colonic fermentation.

Because cow's milk and commercially available infant formulas that are based on cow's milk provide only trace amounts of oligosaccharides, prebiotics can be used to supplement the diet of formula-fed infants. Prebiotics have been defined as non-digestible food ingredients that beneficially affect the host by selectively stimulating the growth and/or activity of one or a limited number of cells in the colon that can improve the health of the host.

Because both the interaction among dietary components and among the microflora of the intestinal ecosystem are very complex, the matrix of an infant formula or other pediatric nutritional supplement may influence the effectiveness of prebiotics and oligosaccharides when such ingredients are provided as supplements in the diet of a formula-fed infant. Moreover, the type and concentration of proteins used in a formula matrix may also modulate the intestinal microbiota. (Boehm et al., *Structural and Functional Aspects of Prebiotics Used in Infant Nutrition*, The Journal of Nutrition.) Because human milk is the preferred source of infant nutrition, it is desirable to provide a formula matrix that mimics the qualities of human milk by allowing for effective supplementation of prebiotics and oligosaccharides as functional food ingredients.

Accordingly, it would be beneficial to provide a nutritional composition for pediatric subjects comprising a nutritional supplement that stimulates the immune system, wherein the supplement is provided in a formula matrix that does not inhibit the beneficial effects of the supplement. Furthermore, it would be beneficial to provide methods for enhancing and improving the immune response of a pediatric subject via administration of a nutritional composition that is well-tolerated by pediatric subjects.

BRIEF SUMMARY

Briefly, therefore, the present disclosure is directed, in an embodiment, to a milk-based nutritional composition for pediatric subjects, comprising a lipid or fat, a protein source and a source of β-glucan. In certain embodiments, the source of β-glucan is a source of β-1,3-glucan. In other embodiments, the source of β-glucan is a source of β-1,3;1,6-glucan. Moreover, in some embodiments, the nutritional composition further includes a source of long chain polyunsaturated fatty acids which include docosahexaenoic acid (DHA) and/or a prebiotic composition which includes a plurality of oligosaccharides such that the overall fermentation rate profile of the prebiotic composition provides an increased population of beneficial bacteria in the human gut over an extended period of time. The prebiotic composition can include a plurality of oligosaccharides, such that at least one of the oligosaccharides has a relatively fast fermentation rate and one of the oligosaccharides has a relatively slow fermentation rate, whereby the combination of the oligosaccharides provides a beneficial overall fermentation rate. In certain embodiments, the prebiotic comprises a combination of galacto-oligosaccharide and polydextrose.

The disclosure is also directed to a nutritional composition comprising, in some embodiments, a milk-based matrix that includes:

a. up to about 7 g/100 kcal of a fat or lipid, more preferably about 3 to about 7 g/100 kcal of a fat or lipid;

b. up to about 5 g/100 kcal of a protein source, more preferably about 1 to about 5 g/100 kcal of a protein source;

c. about 5 to about 100 mg/100 kcal of a source of long chain polyunsaturated fatty acids which include DHA, more preferably about 10 to about 50 mg/100 kcal of a source of long chain polyunsaturated fatty acids which include DHA;

d. about 1.0 to about 10.0 g/L, more preferably about 2.0 g/L to about 8.0 g/L, of a prebiotic composition comprising a plurality of oligosaccharides such that the overall fermentation rate profile of the prebiotic composition provides an increased population of beneficial bacteria in the human gut over an extended period of time; and e. a source of β-glucan.

In yet another embodiment, the invention is directed to a nutritional composition having improved digestibility, the composition comprising a milk-based matrix, a lipid or fat, a protein source, a source of long chain polyunsaturated fatty acids that includes docosahexaenoic acid (DHA), a prebiotic composition which comprises at least 20% of an oligosaccharide mixture comprising polydextrose and galacto-oligosaccharide, and a source of β-1,3-glucan.

In still another embodiment, the present disclosure teaches a method for enhancing immune system function of a pediatric subject by administering β-glucan in a milk-based matrix to the pediatric subject.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

DETAILED DESCRIPTION

Reference now will be made in detail to the embodiments of the present disclosure, one or more examples of which are set forth herein below. Each example is provided by way of explanation of the nutritional composition of the present disclosure and is not a limitation. In fact, it will be apparent to those skilled in the art that various modifications and variations can be made to the teachings of the present disclosure without departing from the scope or spirit of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are obvious from the following detailed description. It is to be understood by one of ordinary skill in the art that the present discussion is a description of exemplary embodiments only and is not intended as limiting the broader aspects of the present disclosure.

"Nutritional composition" means a substance or formulation that satisfies at least a portion of a subject's nutrient requirements.

"Pediatric subject" means a human that is less than 13 years of age. In some embodiments, a pediatric subject refers to a human subject that is less than 8 years old.

"Infant" means a subject ranging in age from birth to not more than about one year and includes infants from 0 to about 12 months corrected age. The term infant includes low birth weight infants, very low birth weight infants, and preterm infants. The phrase "corrected age" means an infant's chronological age minus the amount of time that the infant was born premature. Therefore, the corrected age is the age of the infant if it had been carried to full term.

"Child" means a subject ranging in age from about 12 months to about 13 years. In some embodiments, a child is a subject between the ages of one and twelve years old. In other embodiments, the terms "children" or "child" refer to subjects that are two, three, four, five or six years old. In other embodiments, the terms "children" or "child" refer to any range of ages between about 12 months and about 13 years.

"Children's nutritional product" refers to a composition that satisfies at least a portion of the nutrient requirements of a child.

"Infant formula" means a composition that satisfies at least a portion of the nutrient requirements of an infant. In the United States, the content of an infant formula is dictated by the federal regulations set forth at 21 C.F.R. Sections 100, 106, and 107. These regulations define macronutrient, vitamin, mineral, and other ingredient levels in an effort to stimulate the nutritional and other properties of human breast milk.

"Nutritionally complete" means a composition that may be used as the sole source of nutrition, which would supply essentially all of the required daily amounts of vitamins, minerals, and/or trace elements in combination with proteins, carbohydrates, and lipids.

"Probiotic" means a microorganism with low or no pathogenicity that exerts beneficial effects on the health of the host.

"Prebiotic" means a non-digestible food ingredient that beneficially affects the host by selectively stimulating the growth and/or activity of one or a limited number of bacteria in the digestive tract that can improve the health of the host.

"Effective amount" means an amount that provides a stimulatory immune effect in a subject.

"β-glucan" means all β-glucan, including β-1,3-glucan and β-1,3;1,6-glucan, as each is a specific type of β-glucan. Moreover, β-1,3;1,6-glucan is a type of β-1,3-glucan. Therefore, the term "β-1,3-glucan" includes β-1,3;1,6-glucan.

"Milk-based matrix" means a medium comprising at least one component that has been drawn or extracted from the mammary gland of a mammal. In some embodiments, the milk-based matrix of the disclosed nutritional composition comprises components of milk that are derived from domesticated ungulates, ruminants, humans or any combination thereof. Moreover, in some embodiments, the milk-based matrix comprises casein, whey protein, lactose, or any combination thereof. Further, the milk-based matrix of the present disclosure may comprise any milk-derived or milk-based product known in the art.

The present disclosure describes a nutritional composition for a subject comprising a milk-based matrix, a carbohydrate source, a lipid source, a protein source and a source of β-glucan, especially β-1,3;1,6-glucan, wherein the β-glucan and the milk-based matrix provide a synergistic effect resulting in stimulation of the immune system in a pediatric subject.

The present disclosure also describes a method of enhancing the immune function of a pediatric subject comprising administering an effective amount of a milk-based nutritional composition comprising a carbohydrate source, a lipid source, a protein source and a source of β-glucan.

Suitable fat or lipid sources for practicing the present invention may be comprise any lipid source known in the art, including but not limited to, animal sources, e.g., milk fat, butter, butter fat, egg yolk lipid; marine sources, such as fish oils, marine oils, single-cell oils; vegetable and plant oils, such as corn oil, canola oil, sunflower oil, soybean oil, palmolein, coconut oil, high oleic sunflower oil, evening primrose oil, rapeseed oil, olive oil, flaxseed (linseed) oil, cottonseed oil, high oleic safflower oil, palm stearin, soy lecithin, palm kernel oil, wheat germ oil, medium chain triglyceride Bovine milk protein sources useful in practicing the present invention include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate) and any combinations thereof.

In one embodiment, the proteins are provided as intact proteins. In other embodiments, the proteins are provided as a combination of both intact proteins and partially hydrolyzed proteins, with a degree of hydrolysis of between about 4% and 10%. In certain other embodiments, the proteins are more completely hydrolyzed. In yet another embodiment, the protein source may be supplemented with glutamine-containing peptides.

In a particular embodiment of the invention, the whey:casein ratio of the protein source is similar to that found in human breast milk. In an embodiment, the protein source comprises from about 40% to about 80% whey protein and from about 20% to about 60% casein.

In certain embodiments of the disclosure, the nutritional composition may contain one or more probiotics. Any probiotic known in the art may be acceptable in this embodiment provided it achieves the intended result. In a particular embodiment, the probiotic may be selected from any *Lactobacillus* species, *Lactobacillus rhamnosus* GG, *Bifidobacterium* species, *Bifidobacterium longum*, and *Bifidobacterium animalis* subsp. *lactis* BB-12 or combinations thereof.

If included in the composition, the amount of the probiotic may vary from about $10^4$ to about $10^{10}$ colony forming units (cfu) per kg body weight per day. In another embodiment, the amount of the probiotic may vary from about $10^6$ to about $10^9$ cfu per kg body weight per day. In yet another embodiment, the amount of the probiotic may be at least about $10^6$ cfu per kg body weight per day.

In an embodiment, the probiotic(s) may be viable or non-viable. As used herein, the term "viable", refers to live microorganisms. The term "non-viable" or "non-viable probiotic" means non-living probiotic microorganisms, their cellular components and/or metabolites thereof. Such non-viable probiotics may have been heat-killed or otherwise inactivated, but they retain the ability to favorably influence the health of the host. The probiotics useful in the present invention may be naturally-occurring, synthetic or developed through the genetic manipulation of organisms, whether such new source is now known or later developed.

The nutritional composition contains one or more prebiotics. The term "prebiotic" as used herein refers to indigestible food ingredients which exert health benefits upon the host. Such health benefits may include, but are not limited to, selective stimulation of the growth and/or activity of one or a limited number of beneficial gut bacteria, stimulation of the growth and/or activity of ingested probiotic microorganisms, selective reduction in gut pathogens, and favorable influence on gut short chain fatty acid profile. Such prebiotics may be naturally-occurring, synthetic, or developed through the genetic manipulation of organisms and/or plants, whether such new source is now known or developed later. Prebiotics useful in the present invention may include oligosaccharides, polysaccharides, and other prebiotics that contain fructose, xylose, soya, galactose, glucose and mannose. More specifically, prebiotics useful in the present invention may include polydextrose, polydextrose powder, lactulose, lactosucrose, raffinose, gluco-oligosaccharide, inulin, fructo-oligosaccharide, isomalto-oligosaccharide, soybean oligosaccharides, lactosucrose, xylo-oligosaccharide, chito-oligosaccharide, manno-oligosaccharide, aribino-oligosaccharide, siallyl-oligosaccharide, fuco-oligosaccharide, galacto-oligosaccharide, and gentio-oligosaccharides.

In an embodiment, the total amount of prebiotics present in the nutritional composition may be from about 1.0 g/L to about 10.0 g/L of the composition. More preferably, the total amount of prebiotics present in the nutritional composition may be from about 2.0 g/L and about 8.0 g/L of the composition. At least 20% of the prebiotics can comprise a mixture of galacto-oligosaccharide and polydextrose. The amount of each of galacto-oligosaccharide and polydextrose in the nutritional composition may, in an embodiment, be within the range of from about 1.0 g/L to about 4.0 g/L.

The amount of galacto-oligosaccharide in the nutritional composition may, in an embodiment, be from about 0.1 mg/100 Kcal to about 1.0 mg/100 Kcal. In another embodiment, the amount of galacto-oligosaccharide in the nutritional composition may be from about 0.1 mg/100 Kcal to about 0.5 mg/100 Kcal. The amount of polydextrose in the nutritional composition may, in an embodiment, be within the range of from about 0.1 mg/100 Kcal to about 0.5 mg/100 Kcal. In another embodiment, the amount of polydextrose may be about 0.3 mg/100 Kcal. In a particular embodiment, galacto-oligosaccharide and polydextrose are supplemented into the nutritional composition in a total amount of about at least about 0.2 mg/100 Kcal and can be about 0.2 mg/100 Kcal to about 1.5 mg/100 Kcal.

The nutritional composition of the invention contains a source of long chain polyunsaturated fatty acids (LCPUFAs) that comprises docosahexaenoic acid (DHA). Other suitable LCPUFAs include, but are not limited to, α-linoleic acid, γ-linoleic acid, linoleic acid, linolenic acid, eicosapentaenoic acid (EPA) and arachidonic acid (ARA).

In one embodiment, the nutritional composition is supplemented with both DHA and ARA. In this embodiment, the weight ratio of ARA:DHA may be from about 1:3 to about 9:1. In one embodiment of the present invention, this ratio is from about 1:2 to about 4:1.

The amount of long chain polyunsaturated fatty acids in the nutritional composition is advantageously at least about 5 mg/100 Kcal, and may vary from about 5 mg/100 kcal to about 100 mg/100 kcal, more preferably from about 10 mg/100 kcal to about 50 mg/100 kcal.

The nutritional composition may be supplemented with oils containing DHA and ARA using standard techniques known in the art. For example, DHA and ARA may be added to the composition by replacing an equivalent amount of an oil, such as high oleic sunflower oil, normally present in the composition. As another example, the oils containing DHA and ARA may be added to the composition by replacing an equivalent amount of the rest of the overall fat blend normally present in the composition without DHA and ARA.

If utilized, the source of DHA and ARA may be any source known in the art such as marine oil, fish oil, single cell oil, egg yolk lipid, and brain lipid. In some embodiments, the DHA and ARA are sourced from the single cell Martek oil, DHASCO®, or variations thereof. The DHA and ARA can be in natural form, provided that the remainder of the LCPUFA source does not result in any substantial deleterious effect on the infant. Alternatively, the DHA and ARA can be used in refined form.

In an embodiment of the present invention, sources of DHA and ARA are single cell oils as taught in U.S. Pat. Nos. 5,374,567; 5,550,156; and 5,397,591, the disclosures of which are incorporated herein in their entirety by reference. However, the present invention is not limited to only such oils.

As noted, the disclosed nutritional composition includes a source of β-glucan in each embodiment thereof. Glucans are polysaccharides, specifically polymers of glucose, which are naturally occurring and may be found in cell walls of bacteria, fungi, yeast, and plants. Beta glucans (β-glucans) are themselves a diverse subset of glucose polymers, which are made up of chains of glucose monomers linked together via beta-type glycosidic bonds to form complex carbohydrates.

β-1,3-glucans are carbohydrate polymers purified from, for example, yeast, mushroom, bacteria, algae, or cereals. (Stone B A, Clarke A E. Chemistry and Biology of (1-3)-Beta-Glucans. London:Portland Press Ltd; 1993.) The chemical structure of β-1,3-glucan depends on the source of the β-1,3-glucan. Moreover, various physiochemical parameters, such as solubility, primary structure, molecular weight, and branching, play a role in biological activities of β-1,3-glucans. (Yadomae T., Structure and biological activities of fungal beta-1,3-glucans. Yakugaku Zasshi. 2000; 120:413-431.)

β-1,3-glucans are naturally occurring polysaccharides, with or without β-1,6-glucose side chains that are found in the cell walls of a variety of plants, yeasts, fungi and bacteria. β-1,3;1,6-glucans are those containing glucose units with (1,3) links having side chains attached at the (1,6) position(s). β-1,3;1,6 glucans are a heterogeneous group of glucose polymers that share structural commonalities, including a backbone of straight chain glucose units linked by a β-1,3 bond with β-1,6-linked glucose branches extending from this backbone. While this is the basic structure for the presently described class of β-glucans, some variations may exist. For example, certain yeast β-glucans have additional regions of β(1,3) branching extending from the β(1,6) branches, which add further complexity to their respective structures.

β-glucans derived from baker's yeast, *Saccharomyces cerevisiae*, are made up of chains of D-glucose molecules connected at the 1 and 3 positions, having side chains of glucose attached at the 1 and 6 positions. Yeast-derived β-glucan is an insoluble, fiber-like, complex sugar having the general structure of a linear chain of glucose units with a β-1,3 backbone interspersed with β-1,6 side chains that are generally 6-8 glucose units in length. More specifically, β-glucan derived from baker's yeast is poly-(1,6)-β-D-glucopyranosyl-(1,3)-β-D-glucopyranose.

Moreover, β-glucans have been discovered to have the ability to stimulate the immune system of adults. Indeed, a variety of these polysaccharides have been shown to bind to β-1,3-glucan receptors on monocytes, macrophages, and neutrophils. (Czop, J. K., & Austen, K. F. (1985). β-glucans activate cellular immunity primarily through macrophages and neutrophils. Properties of glycans that activate the human alternate complement pathway and interact with the human monocyte beta glucan receptor. *J. Immuno*. 135, 3388-3393). β-glucan has not, however, been identified as a substance that provides the benefits of the present disclosure and that can be administered to pediatric subjects.

Indeed, the gut microflora of infants is well known to be less developed than that of an adult. While the microflora of the adult human consists of more than $10^{13}$ microorganisms and nearly 500 species, the gut microflora of an infant contains only a fraction of those microorganisms, both in absolute number and species diversity. Because the bacterial populations and species vary immensely between the gut of an infant or child and an adult, it cannot be assumed that a prebiotic substance that has a beneficial effect on adults would also have a beneficial effect on infants and/or children.

As noted, glucans are polysaccharides that belong to a group of physiologically active compounds described as biological defense modifiers. β-1,3;1,6 glucans are a polysaccharide fraction that prime immune surveillance, which may decrease microbial-related illnesses in children or infants by stimulating immune function when administered as part of the nutritional composition of the present disclosure Furthermore, β-glucans are well tolerated and do not produce or cause excess gas, abdominal distension, bloating or diarrhea in pediatric subjects. The efficacy of β-glucan as an immune system stimulator has not previously been demonstrated when the β-glucan is administered simultaneously with a milk-based matrix in order to provide a synergistic, stimulatory immune effect.

In some embodiments, the nutritional composition of the present disclosure comprises β-glucan together with a milk-based matrix, wherein the combination of the two ingredients provides a synergistic effect when incorporated in a nutritional composition. The resulting nutritional composition has a stimulatory effect on a subject's respiratory burst capacity. More specifically, in some embodiments, the combination of β-1,3;1,6-glucan with a milk-based matrix provides the effect of increasing the number of neutrophils in a subject.

When exposed to certain stimuli, phagocytes, including neutrophils, eosinophils, and mononuclear phagocytes, greatly increase their glucose and oxygen consumption and begin to produce large amounts of superoxide ($O_2$) and hydrogen peroxide ($H_2O_2$) in a series of changes known as the "respiratory burst." The oxygen-containing compounds produced by the respiratory burst kill invading bacteria or pathogens in a process called oxygen-dependent intracellular killing. Therefore, stimulating the respiratory burst in a subject enhances the subject's immune system.

To demonstrate this effect, the biological activity of β-glucan in the presence or absence of a milk-based formula may be evaluated in in vivo experiments. One milk-based formula which may be used for experimentation is the commercially available formula Enfagrow® (available from Mead Johnson & Company, Evansville, Ind., U.S.A.). The β-glucan may comprise Wellmune WGP® (available from Biothera, Eagan, Minn., U.S.A.).

For in vivo studies, mice are fed β-glucan (1 mg/mouse/day) either alone or as mixed with a milk-based formula for a maximum of 10 days. Mice similarly fed with saline or with the milk-based formula alone are used as controls. In the murine model, the uptake of oral β-glucan occurs via the Peyer's patches of the small intestine. The particles taken up by the Peyer's patches subsequently enter the systemic circulation, as they are transported via macrophages. Subsequently, degradation occurs in the macrophages, breaking the β-glucan into smaller fragments, which can subsequently activate neutrophils. The total cell numbers are assessed, as are the neutrophil respiratory burst activities, the activation markers on macrophages and on dendritic cells, and cytokine serum levels.

Following oral administration, blood cells are isolated and counted. The cells show that mice treated with formula matrix or β-glucan have significantly higher neutrophil counts on day 10 as compared to PBS untreated mice. These data suggest that β-glucan and formula matrix may stimulate neutrophil mobilization and may play an important role in antimicrobial protective responses. Milk-based formula alone, β-glucan alone and the combination of both increases the number of neutrophils significantly as compared to the controls.

Figure 1:
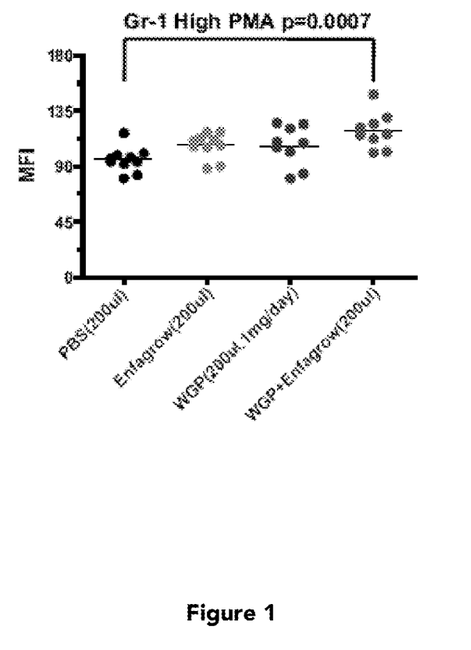
FIG. 1 illustrates the mean fluorescence intensity (MFI) of several samples showing enhanced granulocyte respiratory burst in mice treated with milk-based formula matrix plus WGP glucan as compared to untreated, WGP-glucan-only or matrix-only treated mice.
Figure 2:
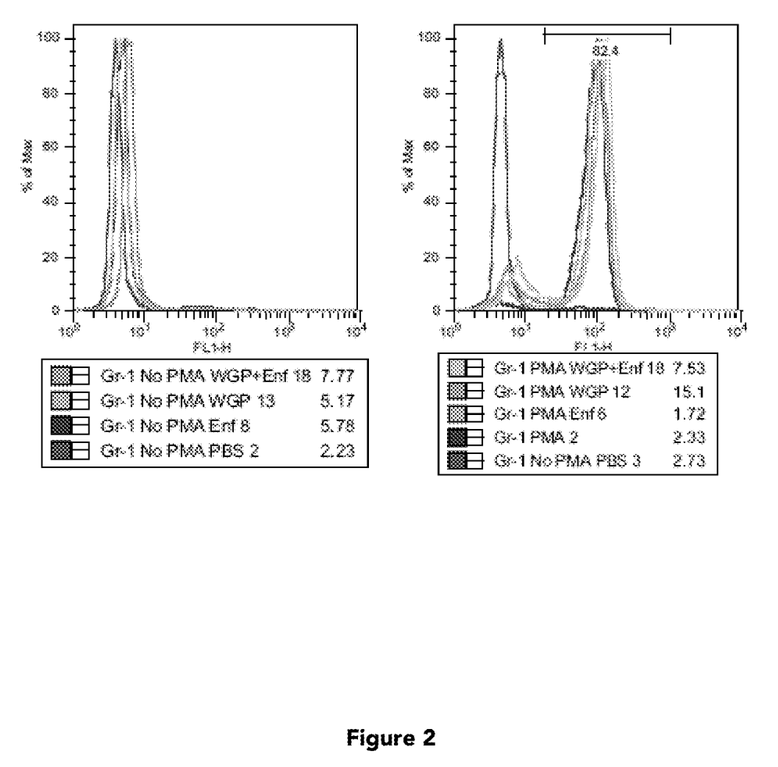
FIG. 2 illustrates the FL1-H fluorescence of several samples showing enhanced respiratory burst in mice treated with milk-based formula matrix plus WGP glucan as compared to untreated or WGP or matrix treated mice.

FIGS. 1 and 2 show the respiratory burst by neutrophils, indicating that there is a synergy between β-glucan and the milk-based matrix, which significantly increases neutrophil respiratory burst. By way of contrast, both β-glucan alone and milk-based formula alone have only a slightly higher respiratory burst effect than the control. Indeed, the combination of β-glucan with a milk-based formula has a synergistic effect on the respiratory burst capacity that is significantly higher than the controls. Moreover, FIGS. 1 and 2 illustrate that β-glucan and milk-based matrix have a synergistic effect of promoting neutrophil respiratory burst.

Figure 3:
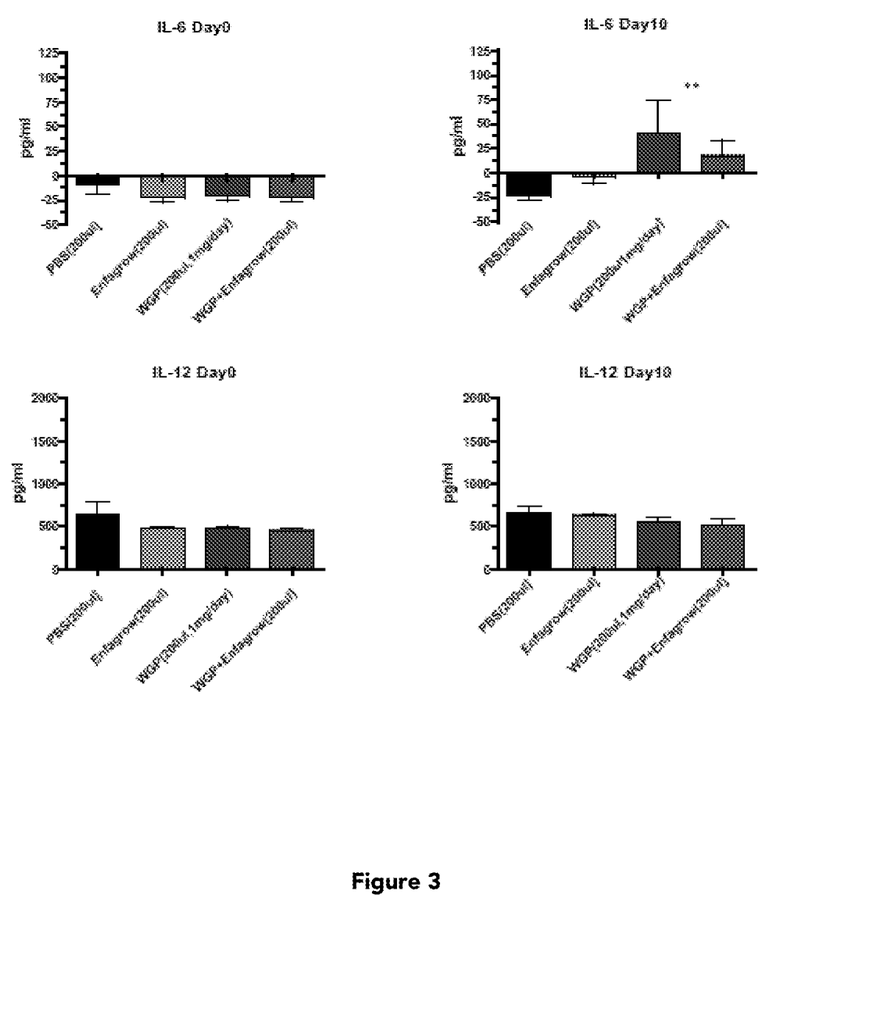
FIG. 3 illustrates elevated IL-6 levels in mice treated with WGP glucan plus milk-based matrix.

As shown in FIG. 3, IL-6 levels are also significantly elevated in mice treated with β-glucan plus formula matrix, as compared to mice receiving milk-based formula alone. FIG. 3 shows that IL-6 is significantly upregulated in mice receiving WGP® β-glucan alone and also by those receiving β-glucan together with milk-based formula as compared to those mice receiving milk-based formula alone.

Thus, in vivo studies demonstrate that orally-administered β-glucan together with a milk-based formula matrix significantly increases peripheral blood neutrophil counts and promotes neutrophil respiratory burst activity. Indeed, there is a synergy between the milk-based formula matrix and β-1,3;1,6-glucan with regards to an aspect of immune cell function, that is, the neutrophil oxidative burst. Furthermore, β-glucan in vivo is able to elicit an increase in IL-6 secretion either in the presence or absence of the milk-based matrix.

Accordingly, addition of β-glucan to a milk-based nutritional composition for a pediatric subject, such as an infant formula or a children's nutritional product, will improve the subject's immune response by increasing resistance against invading pathogens and therefore maintaining or improving overall health. β-1,3;1,6-glucan is able to induce a response by cells of the innate immune system. These in turn can activate adaptive immunity. Therefore, the ability of β-1,3; 1,6-glucan to prime the host immune system by increasing neutrophil cell count and enhancing respiratory burst capacity enhances a subject's immune response.

When administered orally, β-1,3-glucans, such as, for example, β-1,3;1,6-glucan, are not directly absorbed by the metabolic processes of the digestion system. Indeed, significant systemic exposure following yeast β-glucan ingestion does not occur; however, small amounts of insoluble β-glucan particles are taken up by the Peyer's patches of the small intestine, and these particles subsequently enter the systemic circulation, as they are transported via macrophages. Following phagocytosis of β-glucan by macrophages, small fragments of the ingested β-glucan are released from the macrophages. These fragments prime neutrophils and lymphocytes, such as natural killer (NK) cells. Moreover, β-glucan can stimulate cytokine production and may also stimulate T lymphocytes (T cells). This mechanism of action of β-glucan can link the activation of the innate immune system with the activation of adaptive immunity.

Accordingly, in some embodiments, the use of β-1,3-glucan, or more specifically β-1,3;1,6-glucan enhances immune system function. For example, the use of β-1,3;1, 6-glucan may enhance resistance to infection and/or reduce inflammatory responses. In at least one embodiment, the present disclosure is directed to a method for enhancing the immune system function in a pediatric subject comprising administering to the subject a source of β-1,3;1,6-glucan in a milk-based matrix. In another embodiment, the present disclosure is directed to a method for enhancing resistance to infection in a pediatric subject comprising administering to the subject β-1,3;1,6-glucan in a milk-based matrix. In still another embodiment, the present disclosure is directed at a method for reducing the duration and severity of infection caused by a broad spectrum of bacterial and viral pathogens in a pediatric subject comprising administering to a pediatric subject β-glucan in a milk-based matrix. In yet another embodiment, the present disclosure is directed to a method for reducing inflammatory responses accompanying such infections in a pediatric subject comprising administering to the pediatric subject β-glucan in a milk-based matrix.

The nutritional composition of the present disclosure comprises β-1,3-glucan. In some embodiments, the β-1,3-glucan is β-1,3;1,6-glucan. In some embodiments, the β-glucan is whole glucan particle β-glucan, particulate β-glucan, PGG-glucan (poly-1,6-β-D-glucopyranosyl-1,3-β-D-glucopyranose) or any mixture thereof. In other embodiments, the nutritional composition comprises β-1,3;1,6-glucan, which may be provided in the form of whole glucan particles, particulate or microparticulate β-glucan particles or by any combination thereof.

The β-glucan of the present disclosure is an oligomer that resists digestion in the upper gut, meaning that they are minimally degraded by the digestive enzymes of the upper gut. Non-limiting examples of species from which suitable β-1,3;1,6-glucan may be extracted for practice of the present disclosure include *Saccharomyces cerevisiae* (bakers yeast), *Lentinus edodes* (Shitake mushrooms), *Grifola frondosa* (Maitake mushrooms), *Schizophillum commune, Sclerotinia sclerotiorum, Sclerotium glucanicum* and the like. In some embodiments, the β-1,3;1,6-glucan of the present disclosure is isolated from yeasts, mushrooms or other fungi. In one embodiment, the β-glucan is derived from baker's yeast, more particularly, β-glucan obtained from the cell walls of baker's yeast. Likewise, particulate β-1,3;1,6 glucan may be isolated from cell walls of *Saccharomyces cerevisiae*. The β-1,3-glucan with β-1,6-glucan linkage extracted from yeast cells walls acts as a non-specific immune activator. In some embodiments, the nutritional composition of the present disclosure comprises β-glucan consisting of long polymers of β-1,3 glucose with about 3-6% of the backbone glucose units possessing a β-1,6 branch. In other embodiments, the β-glucan may be particulate Wellmune WGP® β-glucan provided by Biothera of Eagan, Minn., USA. In some embodiments, the nutritional composition comprises insoluble β-1,3-glucan with at least one β-1,6-branch.

In an embodiment, the nutritional composition of the present disclosure comprises insoluble β-glucan. Some naturally occurring β-glucans are insoluble in water and may be very large molecules having relatively high molecular weights. Humans are unable to digest carbohydrate polymers with β-glucosidic linkages. Because humans are unable to digest carbohydrate polymers with β-glucosidic linkages, absorption by the intestinal epithelium and significant exposure to particulate yeast β-glucans does not occur. However, some systemic exposure following oral administration does occur and is regulated within the Peyer's patches of the small intestine. The β-glucan absorbed via the Peyer's patches is then transported to the reticuloendothelial system via macrophages. In some embodiments, the β-glucan of the nutritional composition may have been treated with enzymes to reduce its particle size or manipulate its molecular weight.

In some embodiments, the β-glucan of the nutritional composition functions as a prebiotic, which is not digested in the human stomach and small intestine, surviving mainly intact into the colon, at which point it is available for microbial fermentation. In some embodiments, the β-glucan in the nutritional composition may comprise water-soluble, low molecular weight β-glucan. Furthermore, in some embodiments, the nutritional composition may comprise enzymatically treated β-glucans. In still other embodiments, the nutritional composition comprises whole yeast β-glucan particles.

In some embodiments, the nutritional composition of the present disclosure may comprise β-1,3;1,6-glucan as part of a milk-based product for a pediatric subject, such as a children's product or infant formula. In other embodiments, the nutritional composition of the present disclosure may be substantially free of lactose.

In one embodiment, the amount of β-glucan present in the composition is at between about 0.010 and about 0.050 g per 100 g of composition. In some embodiments, the nutritional composition comprises about 10 mg β-glucan per serving. In another embodiment, the nutritional composition comprises between about 5 and about 50 mg β-glucan per serving. In other embodiments, the nutritional composition comprises an amount of β-glucan sufficient to provide about 40 mg β-glucan per day. In some embodiments, β-glucan may be added to the nutritional composition at a concentration sufficient to deliver a target of about 38 mg of β-glucan per day to a subject. The nutritional composition may be delivered in multiple doses to reach a target amount of β-glucan delivered to the subject throughout the day.

In some embodiments, the nutritional composition of the present disclosure may be administered to a pediatric subject in an amount sufficient to deliver an amount of β-glucan ranging from between about 0.5 mg and about 200 mg per day. In another embodiment, the amount of β-glucan administered to a pediatric subject via the nutritional composition may range from about 1 mg to about 100 mg per day. In still another embodiment, the nutritional composition may be formulated to deliver to a pediatric subject between about 20 mg to about 50 mg per day. In yet another embodiment, the amount of β-glucan administered to a pediatric subject via the nutritional composition may be about 35 mg per day.

In another embodiment, the children's product is a milk substitute in the form of a reconstituteable powder to be served 1 to 3 times per day, and the amount of β-glucan administered to a child may range from about 25 to about 50 mg/day of β-glucan. In yet another embodiment, three servings per day of the nutritional composition is recommended for a pediatric subject, with each to deliver a total of from about 25 to about 50 mg/day of β-glucan.

In an embodiment, the nutritional composition comprising β-1,3-glucan is provided as a nutritionally complete infant formula, which contains suitable types and amounts of lipid, carbohydrate, protein, vitamins and minerals. In this embodiment, the amount of carbohydrate may vary from about 8 to about 12 g/100 kcal, with protein from about 1 to about 5 g/100 kcal, lipid or fat from about 3 to about 7 g/100 kcal and may be supplemented with an amount of β-1,3;1, 6-glucan comprising between about 5 and about 577 mg/100 kcal.

Nutritional compositions of the present disclosure may be milk-based, in the form of liquid, evaporated, condensed or dry milk. In some embodiments, the nutritional composition may also include non-dairy liquid or solid food products, protein, flavors or flavor masking agents, sweeteners and vitamins or dietary supplements.

In some embodiments, the nutritional composition may be nutritionally complete, containing suitable types and amounts of lipids, carbohydrates, proteins, vitamins and minerals to be a subject's sole source of nutrition. In one embodiment, the nutritional composition is a children's nutritional product. In another embodiment, the nutritional composition comprises an infant formula. In yet another embodiment, the nutritional composition comprises a nutritionally complete infant formula. In still another embodiment, the nutritional composition comprises a nutritionally complete children's nutritional product.

The disclosed nutritional composition may be provided in any form known in the art, such as a powder, a gel, a suspension, a paste, a solid, a liquid, a liquid concentrate, reconstituteable powdered milk substitute, or a ready-to-use product. The nutritional composition may, in certain embodiments, comprise a nutritional supplement, children's nutritional product, infant formula, human milk fortifier, growing up milk or any other nutritional composition designed for a pediatric subject. Nutritional compositions of the present disclosure include, for example, orally-ingestible, health-promoting substances including, for example, chewable foods, beverages, tablets, capsules and powders. The nutritional composition of the present disclosure may be standardized to a specific caloric content, it may be provided as a ready-to-use product, or it may be provided in a concentrated form.

In embodiments providing a children's nutritional product, one or more vitamins and/or minerals may be added in amounts sufficient to supply the daily nutritional requirements of children between one and thirteen years old. It is to be understood by one of ordinary skill in the art that vitamin and mineral requirements will vary for children between the ages of one and thirteen years. Thus, the embodiments are not intended to limit the nutritional composition to a particular age group but, rather, to provide a range applicable to children between the one and thirteen years old.

In embodiments providing a nutritional composition for a child, the composition may optionally include, but is not limited to, one or more of the following vitamins or derivations thereof: vitamin $B_1$ (thiamin, thiamin pyrophosphate, TPP, thiamin triphosphate, TTP, thiamin hydrochloride, thiamin mononitrate), vitamin $B_2$ (riboflavin, flavin mononucleotide, FMN, flavin adenine dinucleotide, FAD, lactoflavin, ovoflavin), vitamin $B_3$ (niacin, nicotinic acid, nicotinamide, niacinamide, nicotinamide adenine dinucleotide, NAD, nicotinic acid mononucleotide, NicMN, pyridine-3-carboxylic acid), vitamin $B_3$-precursor tryptophan, vitamin $B_6$ (pyridoxine, pyridoxal, pyridoxamine, pyridoxine hydrochloride), pantothenic acid (pantothenate, panthenol), folate (folic acid, folacin, pteroylglutamic acid), vitamin $B_{12}$ (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin $D_3$, 1,25,-dihydroxyvitamin D), vitamin E (α-tocopherol, α-tocopherol acetate, α-tocopherol succinate, α-tocopherol nicotinate, γ-tocopherol), vitamin K (vitamin $K_1$, phylloquinone, naphthoquinone, vitamin $K_2$, menaquinone-7, vitamin $K_3$, menaquinone-4, menadione, menaquinone-8, menaquinone-8H, menaquinone-9, menaquinone-9H, menaquinone-10, menaquinone-11, menaquinone-12, menaquinone-13), choline, inositol, β-carotene and any combinations thereof.

In embodiments providing a children's nutritional product, the composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound.

The minerals can be added to children's nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

In an embodiment, the children's nutritional composition may contain between about 10 and about 50% of the maximum dietary recommendation for any given country, or between about 10 and about 50% of the average dietary recommendation for a group of countries, per serving of vitamins A, C, and E, zinc, iron, iodine, selenium, and choline. In another embodiment, the children's nutritional composition may supply about 10-30% of the maximum dietary recommendation for any given country, or about 10-30% of the average dietary recommendation for a group of countries, per serving of B-vitamins. In yet another embodiment, the levels of vitamin D, calcium, magnesium, phosphorus, and potassium in the children's nutritional product may correspond with the average levels found in milk. In other embodiments, other nutrients in the children's nutritional composition may be present at about 20% of the maximum dietary recommendation for any given country, or about 20% of the average dietary recommendation for a group of countries, per serving.

The children's nutritional composition of the present disclosure may optionally include one or more of the following flavoring agents, including, but not limited to, flavored extracts, volatile oils, cocoa or chocolate flavorings, peanut butter flavoring, cookie crumbs, vanilla or any commercially available flavoring. Examples of useful flavorings include, but are not limited to, pure anise extract, imitation banana extract, imitation cherry extract, chocolate extract, pure lemon extract, pure orange extract, pure peppermint extract, honey, imitation pineapple extract, imitation rum extract, imitation strawberry extract, or vanilla extract; or volatile oils, such as balm oil, bay oil, bergamot oil, cedarwood oil, cherry oil, cinnamon oil, clove oil, or peppermint oil; peanut butter, chocolate flavoring, vanilla cookie crumb, butterscotch, toffee, and mixtures thereof. The amounts of flavoring agent can vary greatly depending upon the flavoring agent used. The type and amount of flavoring agent can be selected as is known in the art.

The nutritional compositions of the present disclosure may optionally include one or more emulsifiers that may be added for stability of the final product. Examples of suitable emulsifiers include, but are not limited to, lecithin (e.g., from egg or soy), alpha lactalbumin and/or mono- and di-glycerides, and mixtures thereof. Other emulsifiers are readily apparent to the skilled artisan and selection of suitable emulsifier(s) will depend, in part, upon the formulation and final product.

The nutritional compositions of the present disclosure may optionally include one or more preservatives that may also be added to extend product shelf life. Suitable preservatives include, but are not limited to, potassium sorbate, sodium sorbate, potassium benzoate, sodium benzoate, calcium disodium EDTA, and mixtures thereof.

The nutritional compositions of the present disclosure may optionally include one or more stabilizers. Suitable stabilizers for use in practicing the nutritional composition of the present disclosure include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, and mixtures thereof.

All percentages, parts and ratios as used herein are by weight of the total formulation, unless otherwise specified.

The nutritional composition of the present disclosure may be substantially free of any optional or selected ingredients described herein, provided that the remaining nutritional composition still contains all of the required ingredients or features described herein. In this context, and unless otherwise specified, the term "substantially free" means that the selected composition may contain less than a functional amount of the optional ingredient, typically less than 0.1% by weight, and also, including zero percent by weight of such optional or selected ingredient.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

As used herein, the term "about" should be construed to refer to both of the numbers specified in any range. Any reference to a range should be considered as providing support for any subset within that range.

The following examples are provided to illustrate some embodiments of the of the nutritional composition of the present disclosure but should not be interpreted as any limitation thereon. Other embodiments within the scope of the claims herein will be apparent to one skilled in the art from the consideration of the specification or practice of the nutritional composition or methods disclosed herein. It is intended that the specification, together with the example, be considered to be exemplary only, with the scope and spirit of the disclosure being indicated by the claims which follow the example.

Examples

Table 1 provides an example embodiment of a powdered nutritional composition according to the present disclosure.

In this embodiment, the weight of corn syrup solids may be adjusted when alternate sources of oligofructose and/or DHA powder are used. Moreover, the powdered nutritional composition described in Table 1 may be reconstituted with water.

TABLE 1

Nutrition profile of an example embodiment of the nutritional composition for a pediatric subject

| DESCRIPTION | AMOUNT PER: 100.0 KG |
|---|---|
| MILK BUTTERMILK POWDER | 31.000 KG |
| MILK WHOLE POWDER INSTANT CODEX | 28.000 KG |
| SUCROSE | 15.000 KG |
| CREAM POWDER COCONUT OIL | 12.600 KG |
| CORN SYRUP SOLIDS | 7.519 KG |
| OLIGOFRUCTOSE | 1.815 KG |
| INULIN | 1.810 KG |
| CALCIUM PHOSPHATE DIBASIC | 0.700 KG |
| FLAVOR VANILLA ARTIFICIAL | 0.582 KG |
| OIL POWDER MARINE HIGH DHA HIGH VIT C | 0.322 KG |
| CORN SYRUP SOLIDS | 145.070 G |
| TAURINE | 22.000 G |
| TOCOPHERYL ACETATE, DL-ALPHA, 50% (DRY, S.D.) | 16.244 G |
| NIACINAMIDE | 7.130 G |
| VITAMIN A PALMITATE, DRY BEADLETS, CW DISPERSIBLE | 3.738 G |
| VITAMIN K1, 1% | 2.546 G |
| VITAMIN D3 POWDER (CHOLECALCIFEROL) | 1.524 G |
| PYROXIDINE HYDROCHLORIDE | 0.540 G |
| THIAMINE HYDROCHLORIDE | 0.534 G |
| CALCIUM PANTOTHENATE | 0.500 G |
| RIBOFLAVIN | 0.114 G |
| FOLIC ACID | 0.060 G |
| IRON TRITURATION Y0034(01) | 0.180 KG |
| CORN SYRUP SOLIDS | 139.441 G |
| FERROUS SULFATE | 36.000 G |
| ASCORBIC ACID WP | 4.509 G |
| MANGANESE SULFATE | 0.050 G |
| CHOLINE BITARTRATE CONDITIONED 80 MESH | 100.000 G |
| MAGNESIUM PHOSPHATE DIBASIC | 80.000 G |
| LACTOSE DRY BLEND | 44.339 G |
| ZINC SULFATE, MONOHYDRATE (PURIFIED BY POWDER) | 12.198 G |
| SODIUM SELENITE S.D. IN CSS | 2.946 G |
| CORN SYRUP SOLIDS BIG-BAG DRB | 2.931 G |
| SODIUM SELENITE ANHYDROUS | 0.015 G |
| COPPER SULFATE ANHYDROUS, EXTRA PURE | 0.295 G |
| MANGANESE SULFATE, MONOHYDRATE | 0.222 G |
| BAKER'S YEAST BETA GLUCAN | 32.000 G |

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. For example, while methods for the production of a commercially sterile liquid nutritional supplement made according to those methods have been exemplified, other uses are contemplated. Therefore, the appended claims should not be limited to the description of the versions contained therein.

What is claimed is:

1. A composition for enhancing immune function in a pediatric subject, wherein the composition is in powder form and comprises:
    a milk-based matrix comprising casein, whey protein, lactose, or any combination thereof;
    3 to 7 g/100 Kcal of a fat source;
    8 to 12 g/100 Kcal of a carbohydrate source;
    1 to 5 g/100 Kcal of a protein source; and
    β-glucan, wherein the β-glucan is insoluble microparticulate β-1,3;1,6-glucan present in an amount of between about 0.010 and about 0.050 g per 100 g of the composition.

2. The nutritional composition according to claim 1, wherein the composition is nutritionally complete.

3. The nutritional composition according to claim 1, further comprising at least one probiotic.

4. The nutritional composition according to claim 1, further comprising at least one additional prebiotic.

5. The nutritional composition according to claim 4, wherein the total amount of the at least one additional prebiotic is from 1.0 g/L to 10.0 g/L of the nutritional composition.

6. The nutritional composition according to claim 4, wherein the at least one additional prebiotic comprises a prebiotic composition comprising galacto-oligosaccharide and polydextrose, wherein the total amount of the prebiotic composition is from 1.0 g/L to 10.0 g/L of the nutritional composition.

7. The nutritional composition according to claim 1, further comprising at least one long chain polyunsaturated fatty acid.

8. The nutritional composition according to claim 7, wherein the at least one long chain polyunsaturated acid comprises docosahexaenoic acid and arachidonic acid in a weight ratio of from 1:3 to 9:1.

9. The nutritional composition according to claim 7, wherein the long chain polyunsaturated fatty acid is selected from the group consisting of docosahexaenoic acid, arachidonic acid, or combinations thereof.

10. A method for stimulating the immune system of a pediatric subject, comprising:
    administering to the pediatric subject a milk-based nutritional composition comprising β-glucan in a milk-based matrix,
    wherein the composition is in a powdered form,
    wherein the β-glucan is insoluble microparticulate β-1,3;1,6-glucan present in an amount of between about 0.010 and about 0.050 g per 100 g of the composition,
    wherein the milk-based matrix comprises casein, whey protein, lactose, or any combination thereof, and
    wherein administration of the nutritional composition stimulates the immune system of the pediatric subject.

11. The method according to claim 10, wherein the milk-based nutritional composition further comprises a probiotic.

12. The method according to claim 10, wherein the milk-based nutritional composition further comprises at least one additional prebiotic.

13. The method according to claim 12, wherein the at least one additional prebiotic comprises a prebiotic composition comprising galacto-oligosaccharide and polydextrose, wherein the total amount of the prebiotic composition is from 1.0 g/L to 10.0 g/L of the nutritional composition.

14. The method according to claim 10, wherein the milk-based nutritional composition further comprises at least one long chain polyunsaturated fatty acid.

15. The method according to claim 10, wherein the milk-based nutritional composition further comprises an infant formula.

16. The method according to claim 10, which comprises a children's nutritional product.

17. A method for increasing the number of neutrophils in a pediatric subject, comprising:
   administering to the pediatric subject a milk-based nutritional composition comprising β-glucan in a milk-based matrix,
   wherein the composition is in a powdered form,
   wherein the β-glucan is insoluble microparticulate β-1,3; 1,6-glucan present in an amount of between about 0.010 and about 0.050 g per 100 g of the composition,
   wherein the milk-based matrix comprises casein, whey protein, lactose, or any combination thereof, and
   wherein administration of the nutritional composition stimulates the immune system of the pediatric subject.

18. The method according to claim 17, wherein the at least one additional prebiotic comprises a prebiotic composition comprising galacto-oligosaccharide and polydextrose, wherein the total amount of the prebiotic composition is from 1.0 g/L to 10.0 g/L of the nutritional composition.

19. The method according to claim 17, wherein administration of the nutritional composition results in a neutrophil burst in the pediatric subject.

20. The method according to claim 17, wherein the milk-based nutritional composition further comprises at least one long chain polyunsaturated fatty acid.

21. The method according to claim 17, wherein the milk-based nutritional composition further comprises an infant formula.

* * * * *

UNITED STATES PATENT AND TRADEMARK OFFICE
CERTIFICATE OF CORRECTION

Page 1 of 1

PATENT NO. : 11,013,759 B2
APPLICATION NO. : 14/833133
DATED : May 25, 2021
INVENTOR(S) : Anja Wittke and Hugh Lipmann It is certified that error appears in the above-identified patent and that said Letters Patent is hereby corrected as shown below:

On the Title Page

At item (73) Assignee, please replace assignee's address "GLENVIEW, ILLINOIS" with
-- Evansville, IN (US) --

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*